(12) United States Patent
Allen (10) Patent No.: US 7,473,264 B2
(45) Date of Patent: Jan. 6, 2009

(54) INTEGRATED LANCE AND STRIP FOR ANALYTE MEASUREMENT

(75) Inventor: John J. Allen, Mendota Heights, MN (US)

(73) Assignee: Lifescan, Inc., Milpitas, CA (US)

( * ) Notice: Subject to any disclaimer, the term of this patent is extended or adjusted under 35 U.S.C. 154(b) by 18 days.

(21) Appl. No.: 11/251,189

(22) Filed: Oct. 14, 2005

(65) Prior Publication Data

US 2006/0030789 A1 Feb. 9, 2006

Related U.S. Application Data

(63) Continuation-in-part of application No. 10/460,030, filed on Jun. 11, 2003, now abandoned.

(60) Provisional application No. 60/458,242, filed on Mar. 28, 2003.

(51) Int. Cl.
*A61B 17/32* (2006.01)

(52) U.S. Cl. ..................................... 606/181

(58) Field of Classification Search ......... 600/575–584, 600/573; 422/56, 82.05; 204/403.01; 435/14; 606/181–183
See application file for complete search history.

(56) References Cited

U.S. PATENT DOCUMENTS

| | | | |
|---|---|---|---|
| 59,308 A | 10/1866 | Wolff | |
| 2,801,633 A | 8/1957 | Ehrlich | |
| 2,896,628 A | 7/1959 | Speelman | |
| 3,030,959 A | 4/1962 | Grunert | |
| 3,046,987 A | 7/1962 | Ehrlich | |
| 3,143,793 A | 8/1964 | Griffiths et al. | |
| 3,626,929 A | 12/1971 | Sanz et al. | |
| 3,741,197 A | 6/1973 | Sanz et al. | |
| 3,831,814 A | 8/1974 | Butler | |
| 4,462,405 A | 7/1984 | Ehrlich | |
| 4,585,446 A | 4/1986 | Kempf | |
| 4,713,165 A | 12/1987 | Conover et al. | |
| 4,753,641 A | 6/1988 | Vaslow | |
| 4,873,993 A | 10/1989 | Meserol et al. | |
| 4,924,879 A | 5/1990 | O'Brien | |
| 5,669,543 A | 9/1997 | Ueno | |
| 5,700,695 A | 12/1997 | Yassinzadeh et al. | |
| 5,708,247 A | 1/1998 | McAleer et al. | |
| 5,820,570 A | 10/1998 | Erickson et al. | |

(Continued)

FOREIGN PATENT DOCUMENTS

EP 0352138 A2 1/1990

(Continued)

OTHER PUBLICATIONS

Somnoplasty Palate Handpiece "A Simple Treatment for Habitual Snoring"; Gyrus ENT, Bartlett, TN 38133, US, 2001 Somnus Medical Technologies, Inc., 1010-2110-05.

*Primary Examiner*—Max Hindenburg
*Assistant Examiner*—Brian Szmal (57) ABSTRACT

The present invention relates, in general, to lancing elements for use in drawing bodily fluids out of a patient and, more particularly, to an improved lancing element including first and second elements positioned relative to each other such that an incision formed by the first element is held open by the second element and bodily fluids are pulled up the lancing element by surface tension on the first and second lancing elements.

11 Claims, 10 Drawing Sheets

U.S. PATENT DOCUMENTS

| | | | |
|---|---|---|---|
| 5,855,801 | A | 1/1999 | Lin et al. |
| 5,857,983 | A | 1/1999 | Radwanski et al. |
| 5,865,744 | A | 2/1999 | Lemelson |
| 5,928,207 | A | 7/1999 | Pisano et al. |
| 5,938,679 | A | 8/1999 | Freeman et al. |
| 5,951,836 | A | 9/1999 | McAleer et al. |
| 5,989,917 | A | 11/1999 | McAleer et al. |
| 6,015,392 | A | 1/2000 | Douglas et al. |
| 6,024,727 | A | 2/2000 | Thorne et al. |
| 6,046,051 | A | 4/2000 | Jina |
| 6,086,545 | A | 7/2000 | Roe et al. |
| 6,139,562 | A | 10/2000 | Mauze et al. |
| 6,153,085 | A | 11/2000 | Patko et al. |
| 6,171,325 | B1 | 1/2001 | Mauze et al. |
| 6,173,202 | B1 | 1/2001 | Eppstein |
| 6,193,873 | B1 | 2/2001 | Ohara et al. |
| 6,241,862 | B1 | 6/2001 | McAleer et al. |
| 6,284,125 | B1 | 9/2001 | Hodges et al. |
| 6,332,871 | B1 | 12/2001 | Douglas et al. |
| 6,364,890 | B1 | 4/2002 | Lum et al. |
| 6,444,115 | B1 | 9/2002 | Hodges et al. |
| 6,475,372 | B1 | 11/2002 | Ohara et al. |
| 6,544,475 | B1 | 4/2003 | Douglas et al. |
| 6,558,528 | B1 | 5/2003 | Matzinger |
| 6,591,124 | B2 | 7/2003 | Sherman et al. |
| 6,607,658 | B1 | 8/2003 | Heller et al. |
| 6,612,111 | B1 | 9/2003 | Hodges et al. |
| 6,620,310 | B1 | 9/2003 | Ohara et al. |
| 6,702,791 | B1 | 3/2004 | Hilgers et al. |
| 6,706,159 | B2 | 3/2004 | Moerman et al. |
| 6,716,577 | B1 | 4/2004 | Yu et al. |
| 6,793,633 | B2 | 9/2004 | Douglas et al. |
| 6,802,199 | B2 | 10/2004 | Hilgers et al. |
| 2001/0056284 | A1 | 12/2001 | Purcell et al. |
| 2002/0082522 | A1 | 6/2002 | Douglas et al. |
| 2002/0168290 | A1* | 11/2002 | Yuzhakov et al. ............. 422/56 |
| 2002/0177761 | A1 | 11/2002 | Ortoff et al. |
| 2002/0177788 | A1 | 11/2002 | Hodges et al. |
| 2003/0018282 | A1 | 1/2003 | Effenhauser et al. |
| 2003/0028125 | A1 | 2/2003 | Yuzhskov et al. |
| 2003/0083686 | A1 | 5/2003 | Freeman et al. |
| 2003/0143113 | A2 | 7/2003 | Yuzhakov et al. |
| 2003/0171699 | A1* | 9/2003 | Brenneman ................. 600/584 |
| 2003/0212345 | A1 | 11/2003 | McAllister et al. |
| 2003/0212347 | A1 | 11/2003 | Sohrab |
| 2004/0096959 | A1 | 5/2004 | Stiene et al. |
| 2004/0106941 | A1 | 6/2004 | Roe et al. |

FOREIGN PATENT DOCUMENTS

| | | |
|---|---|---|
| EP | 1112717 A1 | 7/2001 |
| GB | 2374019 A | 10/2002 |
| WO | WO 95/10221 A | 4/1995 |
| WO | WO 97/19344 A | 5/1997 |
| WO | WO 00/22977 A | 4/2000 |
| WO | WO 01/64105 A | 9/2001 |
| WO | WO 01/87099 A1 | 9/2001 |
| WO | WO 01/72220 A1 | 10/2001 |
| WO | WO 01/73109 A2 | 10/2001 |
| WO | WO 01/73124 A2 | 10/2001 |
| WO | WO 02/06806 A2 | 1/2002 |
| WO | WO 02/24322 A3 | 3/2002 |
| WO | WO 02/49507 A1 | 6/2002 |
| WO | WO 02/50534 A1 | 6/2002 |
| WO | WO 02/100461 A2 | 12/2002 |
| WO | WO 04/041087 A | 5/2004 |
| WO | WO 04/041087 A2 | 5/2004 |

* cited by examiner

INTEGRATED LANCE AND STRIP FOR ANALYTE MEASUREMENT

CROSS-REFERENCE

This is a continuation-in-part application of U.S. application Ser. No. 10/460,030 filed Jun. 11, 2003 now abandoned, which is incorporated herein by reference.

This application claims priority to Provisional Application No. 60/458,242 filed Mar. 28, 2003, which is incorporated herein by reference in its entirety.

BACKGROUND OF THE INVENTION

1. Field of the Invention

The present invention relates, in general, to lancing elements for use in drawing bodily fluids out of a patient and, more particularly, to an improved lancing element including first and second elements positioned relative to each other such that an incision formed by the first element is held open by the second element and bodily fluids are pulled up the lancing element by surface tension on the first and second lancing elements.

2. Description of the Related Art

Integrated skin lancing and bodily fluid analysis samplers are known in the art. One such system is described and illustrated in WO 02/49507. The integrated system described in WO 02/49507 includes a lancing element or lance, which is attached to or integrated with a sensor strip adapted to measure the quantity of an analyte in bodily fluid or, alternatively, some characteristic of the bodily fluid. Usable bodily fluids may include, for example, blood or interstitial fluid (ISF). The lancing element is used to make an incision in the skin and the bodily fluid is drawn up the lancing element to the sensor strip by, for example, capillary action. Such integrated samplers may be combined with, for example, an electrochemical meter and referred to as monolithic or in-situ sampling devices.

Many lancing devices have been devised to form incisions and to enable bodily fluids to be withdrawn from those incisions. Solid lancets are used to open an incision in the skin to allow bodily fluids to escape to the surface of the skin where they can be sampled by the patient or the doctor. In order to ensure that enough fluid is released from the incision, such solid lancing elements are generally larger in diameter to facilitate the flow of sufficient bodily fluids from the incision for sampling purposes. However, such solid needles generally rely on the size of the incision to ensure that enough bodily fluids are expressed and are not used to facilitate the flow of fluids to the testing apparatus.

Hollow needles have also been described for use in drawing fluids out of the body for testing purposes; such needles may have a pointed or beveled end to facilitate opening the incision. In such needles, the incision is held open by the outer diameter of the needle to facilitate the flow of bodily fluids out of the incision and the bodily fluids are drawn up the needle either by a vacuum or by capillary action or by a combination of vacuum and capillary action.

Other lancing devices have been described wherein the lance is a flat or partially curved piece which includes an open channel for guiding fluid from the sharpened tip to the proximal end of the lance by means of, for example, surface tension and/or capillary action. Such lancing elements are advantageous because of the ease of manufacture and the ease of integrating them into, for example, a sensor strip, in order to facilitate both lancing and measurement in a single element. Where the landing element is a flat or partially flat piece which includes an open channel for guiding fluid, it is possible for the edges of the incision to close on the channel, fully or partially blocking the channel and preventing bodily fluids from flowing to the proximal end of the channel or limiting the amount of fluid which can flow.

Problem to be Solved

It would, therefore, be advantageous to design a lancing device where the lancing element is a flat or partially curved piece including an open channel and the lancing element includes a separation element for holding the incision open when the lancing element is in the wound and preventing the edges of the incision from closing on the lancing element and partially or fully blocking the open channel. It would be advantageous to design a lancing device wherein the separation element is positioned slightly proximal to the sharpened tip of the lancing element to facilitate insertion of the lance into the skin. It would further be advantageous to design a lancing device wherein the lancing element and the separation element are formed from a single metal sheet. It would further be advantageous to design a lancing device wherein the lancing element and the separation element are positioned opposite each other such that fluid is pulled up the lancing element and into the open channel by surface tension between the fluid and the lancing element and separation element, thus facilitating the filling of the channel. It would further be advantageous to design a lancing device wherein the lancing element and the separation element are formed from a single sheet of metal rolled to position the separation element opposite the lancing element such that the proximal end of the lancing element and the separation element form an open channel. It would further be advantageous to manufacture the lancing devices described herein using, for example, a metal forming or stamping process.

SUMMARY OF THE INVENTION

A lance according to the present invention includes a lancing element having a first sharpened end point, a separation element having a second sharpened end point wherein the second sharpened end point is positioned proximal to the first sharpened end point, a connector connecting a proximal portion of the first lancing element to a proximal portion of the separation element, the connector forming a channel. In a further embodiment of the present invention, the separation element is positioned at an angle to the lancing element. In a further embodiment of the present invention the lancing element, the separation element and the channel are formed from a single sheet of metal. In a further embodiment of the present invention, a space between the lancing element and the separation element forms a gap, the gap increasing in size proximal to the second sharpened tip. In a further embodiment of the present invention, at least a portion of the channel is treated with a hydrophilic surface coating. In a further embodiment of the present invention, at least a portion of the lancing element and at least a portion of the separation element are coated with a hydrophilic surface coating. In a further embodiment of the present invention, a proximal end of the channel is integrated into a sensor strip. In a further embodiment of the present invention, the sensor strip is connected at a proximal end thereof to a plurality of additional sensor strips

BRIEF DESCRIPTION OF THE DRAWINGS

While the novel features of the invention are set forth with particularity in the appended claims, a better understanding of the features and advantages of the present invention will be obtained by reference to the following detailed description that sets forth illustrative embodiments, in which the principles of the invention are utilized, and the accompanying drawings of which:

DETAILED DESCRIPTION OF ILLUSTRATIVE EMBODIMENTS OF THE INVENTION

Figure 1:
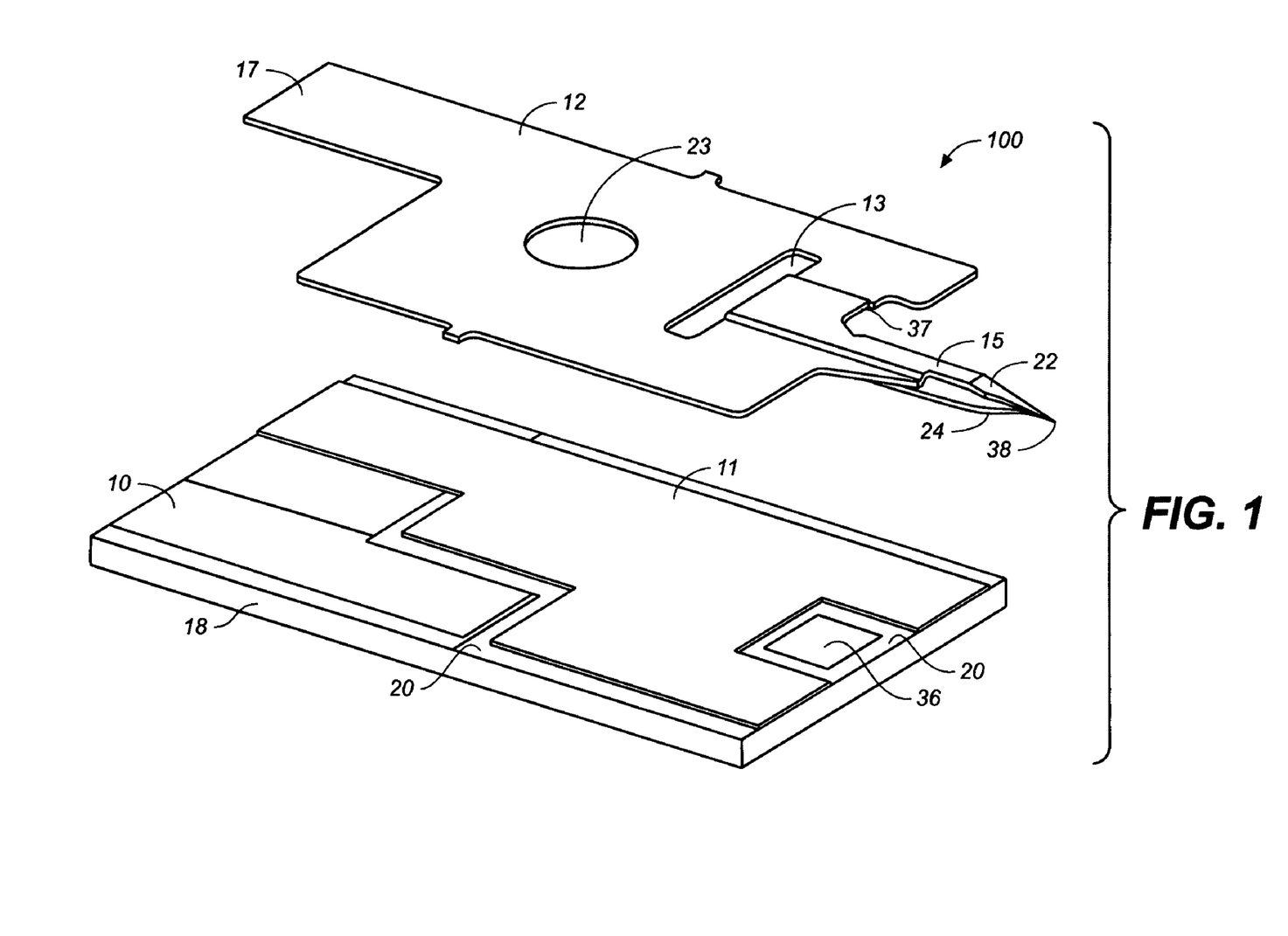
FIG. 1 is a perspective view of a lancing element and sensor strip according to the present invention.

FIG. 1 is a perspective view of lance 15 and sensor strip 100 according to the present invention. In FIG. 1, lance 15 is connected to sensor strip 100. Sensor strip 100 may be, for example, a glucose sensor strip which uses electrochemistry to measure the amount of glucose in a bodily fluid, such as, for example, blood or interstitial fluid. Additionally, sensor strip 100 may be, for example, a coagulation sensor which measures a physical characteristic of a bodily fluid such as viscosity, capacitance, resistance, and the like. In FIG. 1, lance 15 further includes lancing element 22 and separation element 24. Sensor strip 100 further includes first electrode contact 10, adhesive layer 11, conductive substrate 12, vent hole 13, second electrode contact 17, insulating substrate 18, insulating layer 20, registration hole 23 and working electrode 36. In an embodiment of the invention, sensor strip 100 may have an approximate width of 0.22 inches and an approximate length of 0.55 inches.

Figure 2:
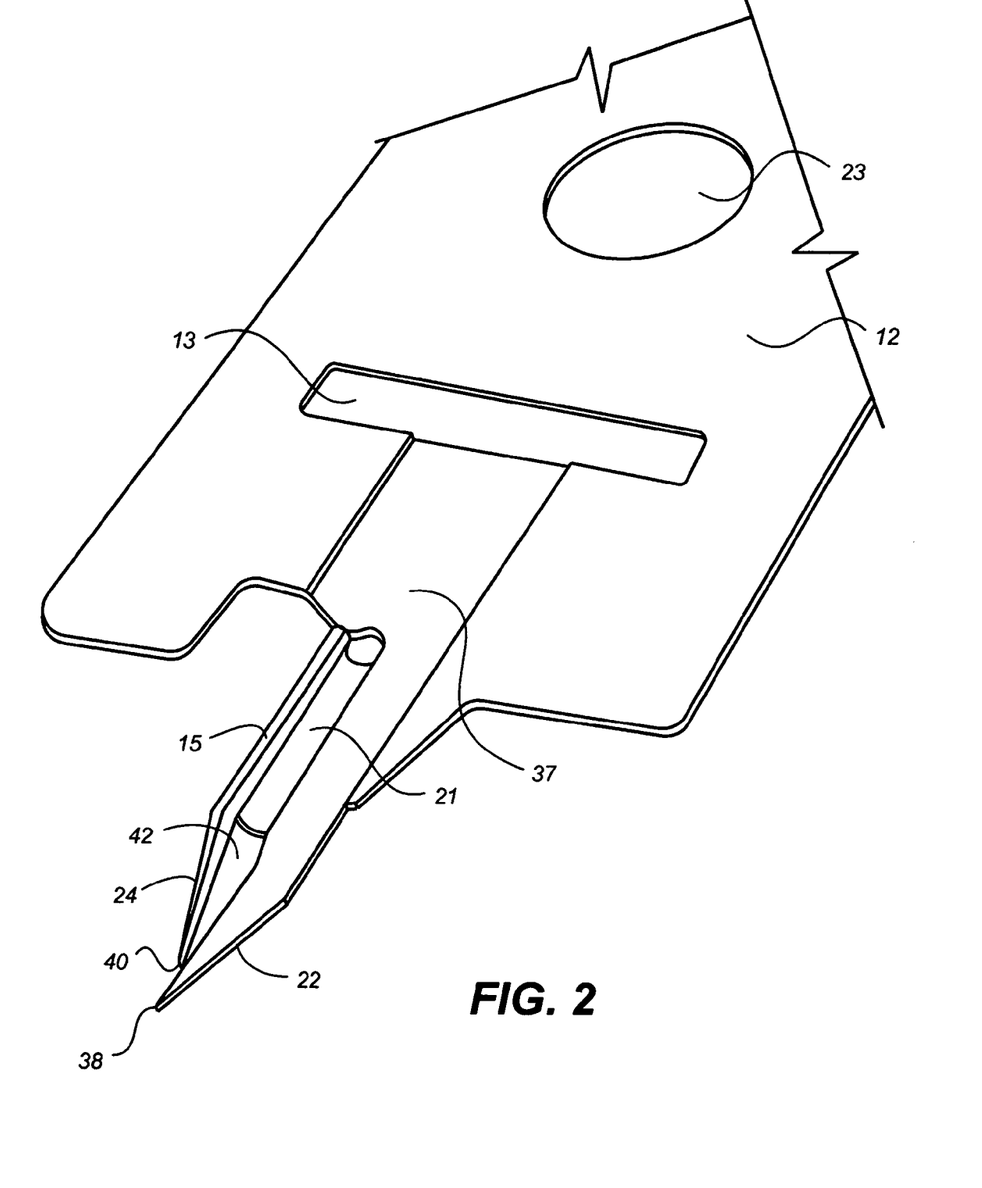
FIG. 2 is a perspective view of the top layer of a lancing element according to the present invention.

FIG. 2 is a perspective view of lance 15 and the top layer of sensor strip 100 for use in the present invention. In FIG. 2, the top layer of sensor strip 100 and lance 15 is formed from conductive substrate 12. In the embodiment illustrated in FIG. 2, conductive substrate 12 includes vent hole 13 and registration hole 23. In FIG. 2, lance 15 includes lancing element 22, separation element 24 and fill channel 21.

One embodiment of a lancing element and sensor strip suitable for use in the present invention may be described with reference to FIGS. 1 and 2. In the embodiment illustrated in FIGS. 1 and 2, sensor strip 100 includes first electrode contact 10, wherein first electrode contact 10 may be screen printed on an insulating substrate 18, and a second electrode contact 17, wherein second electrode contact 17 comprises a portion of conductive substrate 12 which is contiguous with reference electrode 37 and lance 15. In the embodiment of the lancing element and sensor strip illustrated in FIGS. 1 and 2, the orientation of first electrode contact 10 and second electrode contact 17 are arranged such that an analyte measurement meter, such as, for example, a glucose meter (not shown) can establish electrical contact with sensor strip 100. In the illustrated embodiment, first electrode contact 10 and second electrode contact 17 are arranged on the same side of insulating substrate 18 to facilitate contact of both electrodes at the distal end of sensor strip 100.

Sensor strip 100 is manufactured using adhesive layer 11 to attach insulating substrate 18 to conductive substrate 12. Adhesive layer 11 could be implemented in a number of ways, including using pressure sensitive material, heat activated material, or UV cured double sided adhesive material. Conductive substrate 12 may be, for example, a sheet of electrically conductive material such as gold or plated stainless steel. The geometry of conductive substrate 12 may be formed by, for example, stamping process or photo etching. In the embodiment illustrated in FIGS. 1 and 2, lance 15 may be manufactured as an integral part of conductive substrate 12. Vent hole 13, may be formed by, for example, punching through conductive substrate 12. Vent hole 13 is used to facilitate the transport of bodily fluid up lance 15 and across working electrode 36. Registration hole 23 may be formed during the stamping process of making conductive substrate 12.

In one embodiment of the invention, an analyte sensing layer may be, for example, a glucose sensing layer, including an enzyme, a buffer, and a redox mediator. An analyte sensing layer (not shown) may preferably be deposited on top of working electrode 36. Where an analyte sensing layer is used to detect the presence and concentration of glucose in a bodily fluid, at least a portion of glucose sensing layer dissolves in the bodily fluid and is used to convert the glucose concentration into an electrically measured parameter which is proportional to the glucose concentration in the sample.

In the embodiment illustrated in FIGS. 1 and 2, lance 15 has a distal and a proximal end and the proximal end is integrated with reference electrode 37 and the distal end includes sharpened tip 38 at the distal end of lacing element 22. Lance 15 may be formed by the process of stamping or photo-etching a conductive metal sheet. Photo-etching lance 15 is also beneficial in facilitating the manufacture of a lancing element which has a sharp lancing element 22 and separation element 24. In a subsequent process step, lance 15, lancing element 22, and separation element 24 may be bent to form a "V" or "U" shaped channel geometry as shown in FIG. 2. Fill channel 21 serves as a conduit from lancing element 22 and separation element 24 to working electrode 36 and reference electrode 37. In one embodiment of the present invention, the distal end of lacing element 22 and separation tip 40 of separation element 24 are offset by about 0.005 inches to 0.020 inches.

The design of lance 15 is adapted to more effectively cut skin due to a sharper leading point of lancing element 22. As illustrated in FIG. 2, with separation tip 40 offset distally from sharpened tip 38 of element 22, the extreme distal end of lance 15 comprises only sharpened tip 38 which may be a very sharp point or edge to facilitate the initial incision as lancing element 22 enters the skin. In contrast, if lancing element 22 and separation element 24 were coincident, the leading point of lance 15 would include both sharpened tip 38 and separation tip 40 making the combination less sharp than the embodiment illustrated in FIG. 2 and requiring more force to create the initial incision. The offset of sharpened tip 38 and separation tip 40 make lance 15 more manufacturable because it reduces the inherent alignment difficulties in bringing the sharp point of lancing element 22 and separation element 24 into alignment or contact with each other. The embodiment of the invention illustrated in FIGS. 1 and 2 is further beneficial because it enhances fluid egress by helping to spread and hold open the skin wound after the initial incision is made. In the embodiment illustrated in FIGS. 1 and 2, the lance 15 further includes reference electrode 37 and second electrode contact 17. Alternative embodiments may include forming all of the electrodes and electrode contacts on insulating substrate 18.

In the embodiment of the invention illustrated in FIG. 2, lance 15 includes fill channel 21, wherein the seamless transition between the lancing element 22 and separation element 24; and fill channel 21 facilitates the flow of bodily fluid from the wound to working electrode 36. Additionally, the seamless transition between the lancing element 22, separation element 24 and fill channel 21 prevents the introduction of stop junctions which can impede the capillary flow rate of liquid samples. The unique geometry increases the likelihood that a liquid sample will sufficiently cover working electrode 36 and reference electrode 37 regardless of the height of the lance 15 above or below the skin wound, or even if lance 15 lies horizontally offset from the wound. In certain embodiments of the invention, sample can be applied to the side of lance 15 rather than just the proximal end of lance 15 which provides a user the option of dosing sample onto sensor strip 100 after a site has been lanced separately.

In the embodiment of the invention illustrated in FIG. 2, the gap 42 between lancing element 22 and separation element 24 guides bodily fluids into fill channel 21. The increasing separation between lancing element 22 and separation element 24 as fluid moves distally towards fill channel 21 facilitates the drawing of fluid into fill channel 21 and from fill channel 21 to sensor strip 100. As gap 42 narrows towards a distal end of separation tip 40 of separation element 24, the surface tension between the bodily fluid in gap 42 and the walls of gap 42 increases, thus bodily fluid is drawn more readily into gap 42, and up into sensor strip 100. Gap 42 is also advantageous in that it facilitates the introduction of bodily fluids into fill channel 21 by facilitating the flow of bodily fluids positioned to the side of gap 42, thus enhancing the ways in which sensor strip 100 may be used to gather bodily fluids.

Fill channel 21 may facilitate the flow of bodily fluids by, for example, wicking or capillary action. In the embodiment illustrated in FIGS. 1 and 2, fill channel 21 has an open geometry which facilitates the wicking of viscous samples and provides for simpler manufacturing techniques when compared with closed capillary channels. For certain embodiments of the invention, fill channel 21 may be coated with a surfactant coating or undergo a hydrophilic surface treatment to increase the capillary force within fill channel 21. For certain embodiments of the invention separation element 24 and lancing element 22 may be coated with a surfactant coating or undergo hydrophilic surface treatment to increase the capillary flow force within gap 42. Additionally, the open geometry of fill channel 21 facilitates the wicking of sample because it prevents the formation of a vacuum block. In a closed channel geometry, a capillary inlet can become plugged if it is positioned too close to the wound or inside the wound preventing air from facilitating the flow of sample to the capillary. With the open geometry of fill channel 21, the proximal end of lance 15 can be positioned arbitrarily close to the source of the blood and allow for sufficient fill of sample. In this embodiment of the invention, the open geometry of fill channel 21 has the capacity to hold a larger sample volume than the minimum sample volume to cover reference electrode 37 and working electrode 36. The open geometry of fill channel 21 thus allows excess sample to accumulate along fill channel 21 which helps leave a cleaner wound site.

In the illustrated embodiment as shown in FIG. 2, the geometry of reference electrode 37 may be formed during the stamping process which effectively embosses the surface of conductive substrate 12. The stamping process may provide the pressure needed to create a recess in conductive substrate 12 which can help define the distance between reference electrode 37 and working electrode 36. For certain applications of the described invention, it may be advantageous to control the distance between reference electrode 37 and working electrode 36 by embossing conductive substrate 12 instead of controlling the thickness of adhesive layer 11. For other applications of the described invention, it may also be advantageous to not emboss the conductive substrate 12 and use adhesive layer 11 to help define the geometry of reference electrode 37.

In the embodiment of sensor strip 100 illustrated in FIG. 1, insulating substrate 18 consists of material such as polyester or ceramic on which a conductive material can be printed onto insulating substrate 18 through silk-screening, sputtering, or electro-less deposition. Conductive material deposited on insulating substrate 18 forms first electrode contact 10 and working electrode 36. Insulating layer 20 may be, for example, screen printed to form a boundary for first electrode contact 10 and working electrode 36.

Figure 3:
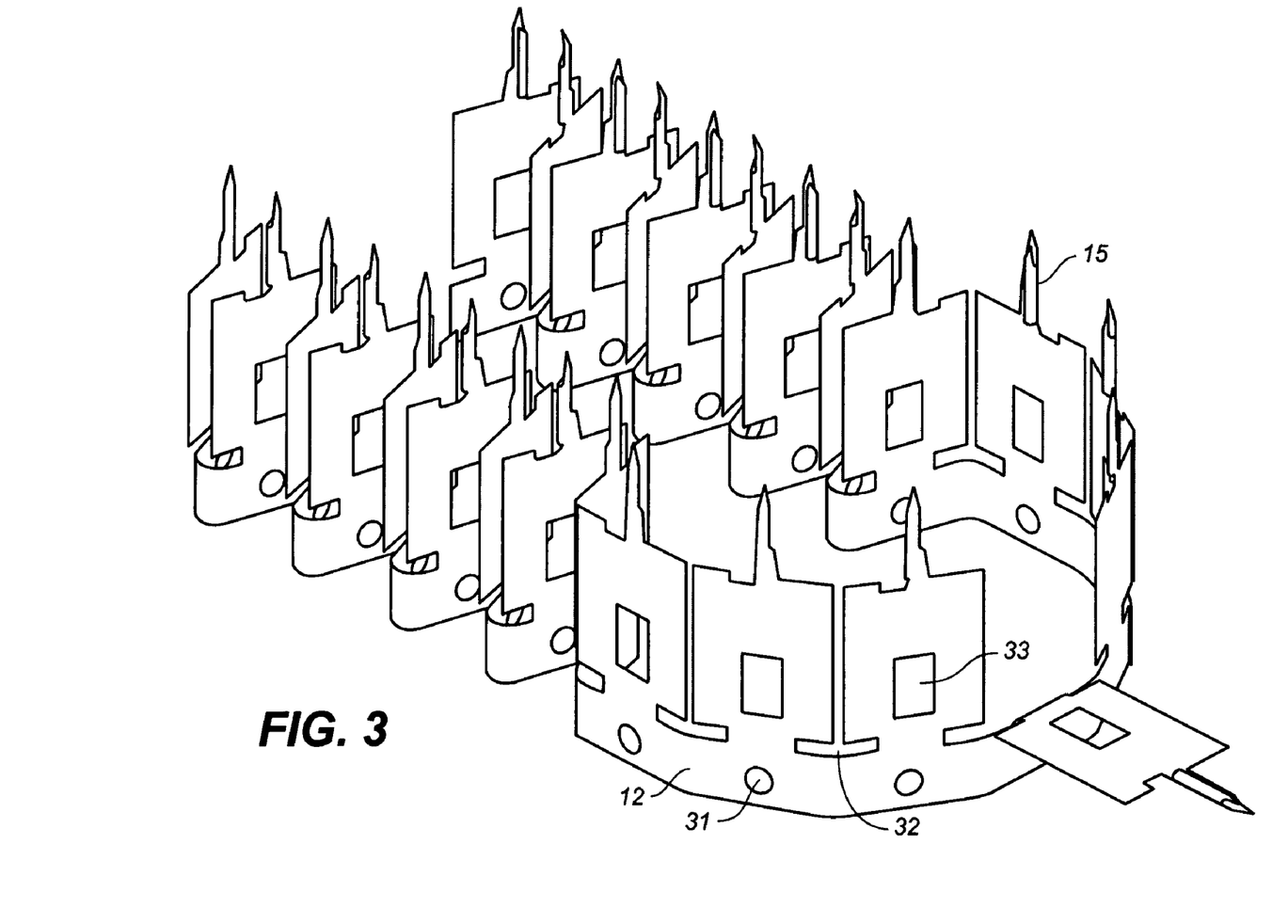
FIG. 3 is a perspective view of another embodiment of the invention in which multiple sensor strips form an array of sensors for use in a cartridge format.

FIG. 3 is a perspective view of another embodiment of the invention in which multiple sensor strips form an array of sensors for use in a cartridge format. Such an array may be inserted into a meter (not shown) having sensor strips dispensed in a serial manner, one by one. The format of this embodiment allows a row of sensor strips to be folded in a manner similar to an accordion wherein several sensor strips similar to sensor strip 100 in FIG. 1 are attached together on an arrangement which facilitates their use in a cartridge. In FIG. 3, conductive substrate 12 is stamped in a progressive manner to form lance 15 such that several of them are chained together in series. The stamping process of conductive substrate 12 forms index hole 31, neck 32, and contact hole 33.

In a further embodiment of the invention, a second electrode layer (not shown) comprising an adhesive layer and glucose sensing layer would be attached to conductive substrate 12 as illustrated in FIG. 3. A contact area for a reference electrode for all of the sensor strips within the array may be formed using a single area within conductive substrate 12. However, individual contacts must be made for working electrode 36 for all of the sensor strips within the array. In the embodiment of this invention, index hole 31 is used to index the sensor strip cartridge so that it can move a fresh sensor strip to a test position. Neck 32 is punched in between two adjacent sensor strips. The purpose of neck 32 is to facilitate the sensor strip bending at the location of neck 32. In order for the sensor strip to be expressed such that a user can apply blood, the sensor strip is bent downward and neck 32 facilitates bending at a defined location. Contact hole 33 on conductive substrate 12 allows electrical contact to be made with a working electrode on an insulating substrate.

In a method of lancing in accordance with the present invention, a lance similar to the embodiments illustrated in FIGS. 1 through 3 is provided having a lancing element 22 with a sharpened tip 38, a separation element 24 having a separation tip 40 is positioned proximal to sharpened tip 38. In one embodiment of the invention the separation tip 40 may be positioned between approximately 0.005 inches and 0.020 inches proximal to sharpened tip 38. A method according to the present invention further includes the step of providing a connector connecting the proximal end of lancing element 22 to the proximal end of separation element 24 wherein the connector forms a fill channel 21 extending from the proximal end of lancing element 22 and the proximal end of separation element 24 to a working electrode 36 of sensor strip 100. The method further including the steps of inserting the lancing element into skin to form an incision, inserting the separation element 24 to further open the incision and maintaining the position of the lancing element 22 and the separation element 24 in the incision while blood or other bodily fluids are drawn into a gap 42 between the lancing element 22 and separation element 24. The method further comprising the step of drawing the bodily fluids from gap 42 into fill channel 21.

A lance 15 constructed in accordance with the present invention is beneficial due to the seamless transition between the tip section and the capillary section, and because the tip itself is a type of capillary. The unique construction of this design better insures that bodily fluids enter the fill channel 21 regardless of the height of the tip above or below the skin wound, or even if the tip lies horizontally offset from the wound, where the lance acts as a conduit for the bodily fluids.

A sensor strip 100 constructed according to the present invention is more easily by manufactured than a closed channel sensor strip. Such a sensor strip may be manufactured by, for example, injection molding, embossing, or chemical etching, or even simple machining. While the capillary force of an open channel may be weaker than a comparable closed channel, the weakness can be overcome with the use of, for example, hydrophilic surface treatments or surfactant coatings including: Tween-80, a product of Sigma Chemical Co., St. Louis, Mo.; Aerosol OT a product of Cytec Industries, West Paterson, N.J.; JBR-515, a product of Jeneil Biosurfactant Company of Saukville, Wis.; and Niaproof a product of Sigma Chemical Co., St. Louis, Mo.

A sensor strip 100 constructed according to the present invention may have improved transfer properties because the invention described herein prevents the creation of a vacuum block in fill channel 21 that would prevent fluid from moving through the fill channel 21 and onto the measurement pad. With a closed channel capillary, the inlet must be positioned or designed to ensure that air is not prevented from freely entering the capillary during transfer into the measurement area. Thus, in a closed channel system, if the inlet is positioned too close to the wound or even inside it, flow may be disrupted or stopped. With the open channel of a sensor strip designed in accordance with the present invention, however, the inlet to the channel can be positioned arbitrarily close to the source of the blood.

Another advantage of a sensor strip in accordance with the present invention including an open channel is that such a sensor strip has the capacity to hold a larger volume of fluid than the minimum required to fill and initiate transfer into the measurement pad. One embodiment of the present invention the minimum volume required to fill the lance such that the column of fluid reaches the measurement pad is approximately 230 nL. However, lancing may produce quantities which are greater than 230 nL. Because of the open channel form in the present invention, the excess blood that is presented to the lance will continue to accumulate along the lance channel, forming a bulging drop of blood. This property is useful in that it clears away excess blood from the skin, leaving a cleaner lance wound.

Another advantage of the open channel design in accordance with the present invention is that a drop of fluid can be applied to the side of the lance rather than just at the tip of the lance (i.e. in a closed channel there is a distinct area where fluid must be presented to be drawn into the capillary. Manual application of blood might be required if the blood comes from a site that has been lanced separately. Thus, using a sensor strip designed in accordance with the present invention, provides the option of 'side' filling increases the user's options.

In one embodiment of the present invention, the stamped metal of conductive substrate 12 could also serve as a working or counter electrode. A unique aspect of the sheet metal design used in the present invention is the fact that it also allows the assembly to be constructed with first electrical contact 10 and second electrode contact 17 on the same side of the sensor strip. This greatly simplifies the requirements for mating contacts on a meter because conductive substrate 12 comprises a solid conductor allowing electrical contact to be established from both the top and bottom side of conductive substrate 12, wherein the top side of conductive substrate 12 is on the same side as second electrical contact 17 and the bottom side of conductive substrate is on the same side as reference electrode 37.

On a conventionally constructed electrochemical sensor strips using a facing electrode arrangement where both working and reference electrodes are printed or applied onto an insulating substrate, the electrical contacts must be positioned on opposites sides of the sensor strip making the meter contacts more complex. If reference electrode 37 was printed or applied onto an insulating substrate, conductive substrate 12 would be insulated on the top side preventing electrical connection to be established from the top side. It could be possible to establish electrical connection from the top side if there was a partial removal of insulation from conductive substrate 12, however, this would add additional complexity to the manufacturing of the sensor strip.

Finally, because sheet metal forming can be done as a progressive die stamping, in a sensor strip designed in accordance with the present invention with individual lances chained together in series, it could be possible to construct an array of test sensors with a single, common reference thus requiring just one contact.

Figure 4:
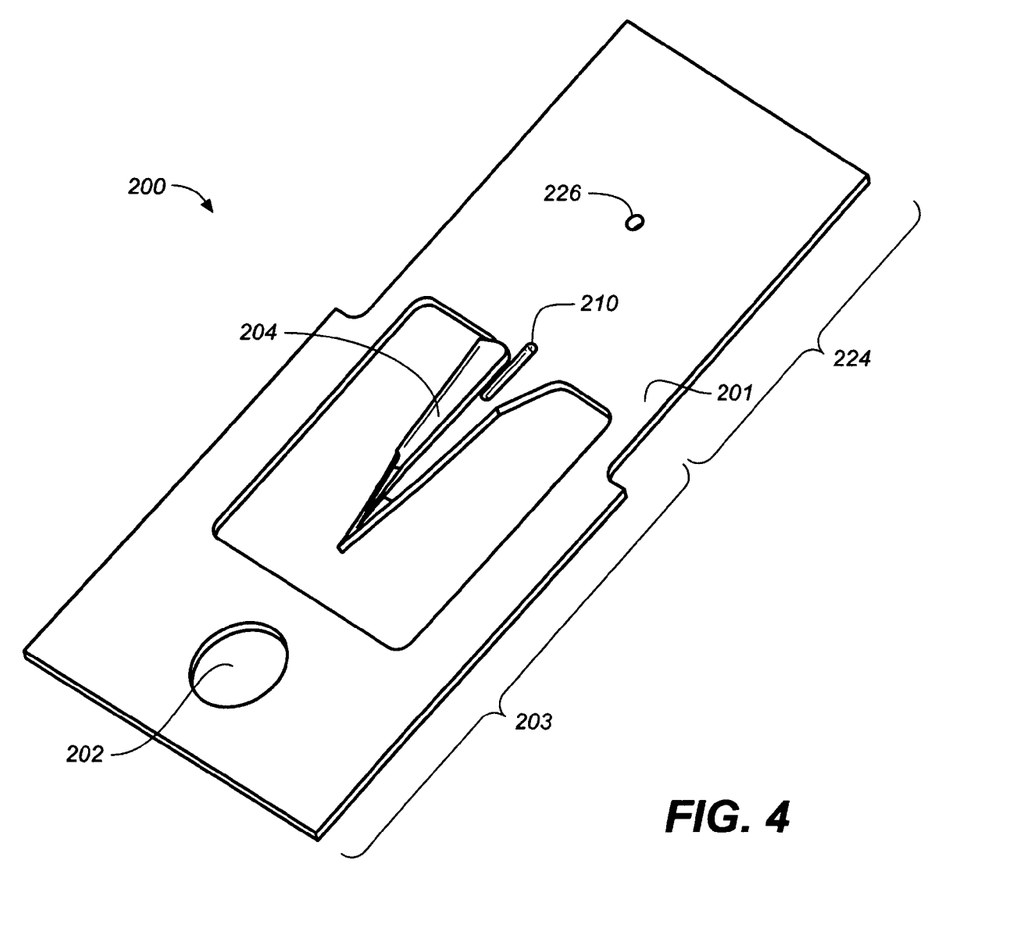
FIG. 4 is a bottom perspective view of a top layer having a lance according to another embodiment of this invention.
Figure 5:
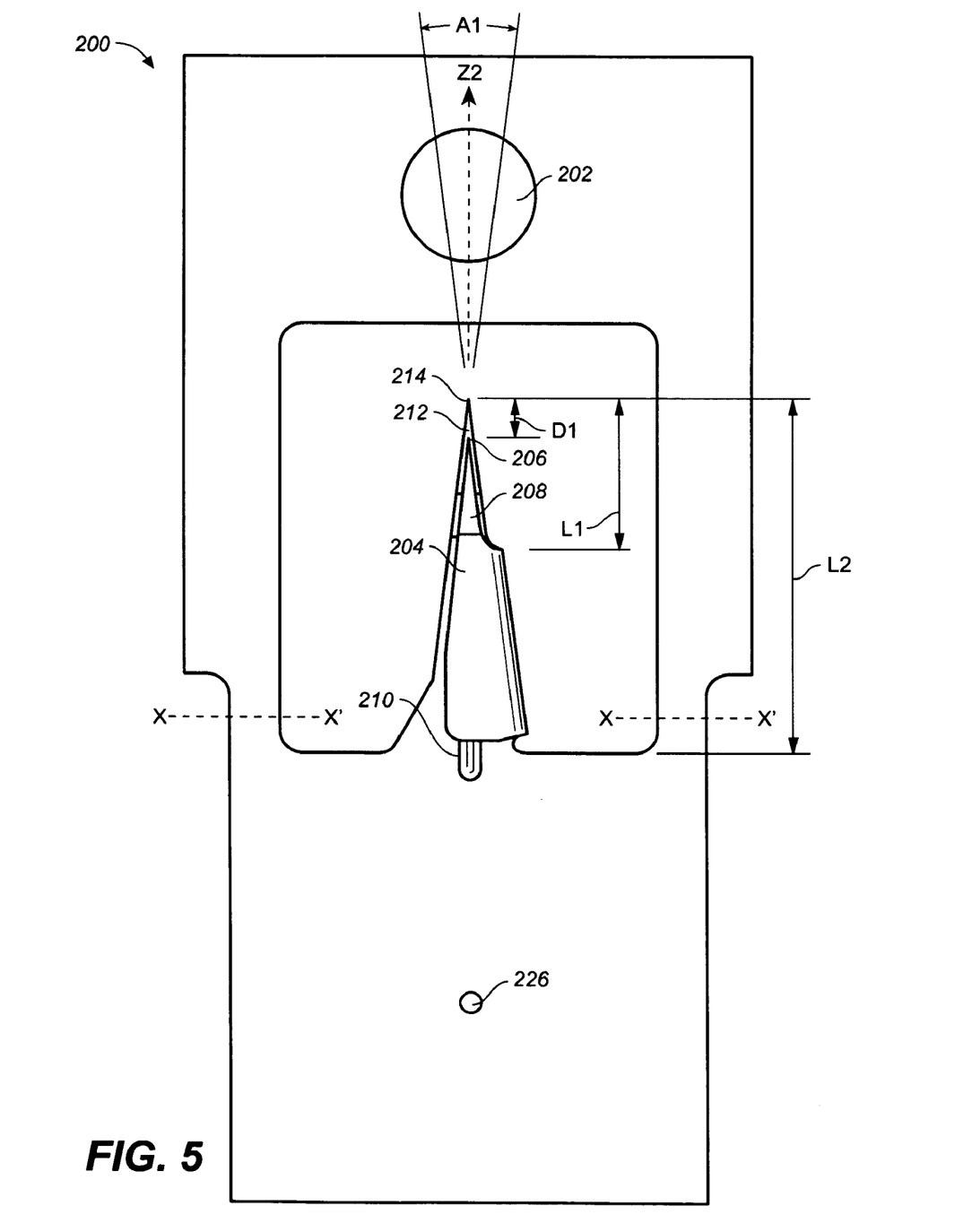
FIG. 5 is a bottom plan view of the top layer and the lance in accordance with the embodiment shown in FIG. 4.
Figure 7:
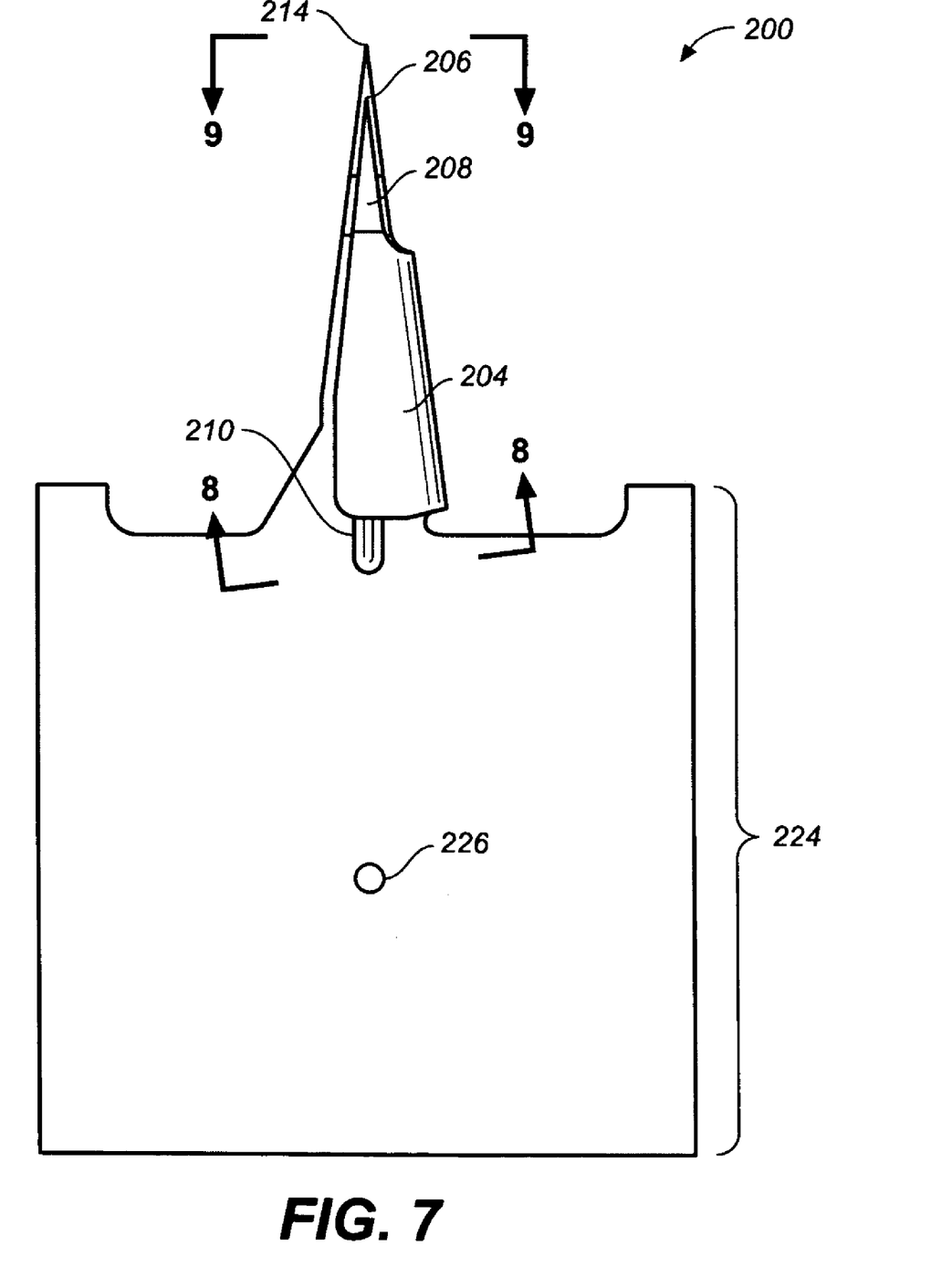
FIG. 7 is a bottom plan view of the top layer in which a handle portion was removed in accordance with the embodiment shown in FIG. 4.

FIG. 4 is a bottom perspective view of a top layer 200 according to another embodiment of this invention. In FIG. 4, top layer 200 includes a conductive substrate 201, a handle portion 203, a main body 224, a hole 202, a vent hole 226, and a lance 204. Conductive substrate 201 may be a material called "stainless steel 301" in the form of a sheet having about a 0.003 inch thickness. Handle portion 203 and hole 202 may be used to immobilize and register top layer 200 when it undergoes a stamping process. Handle portion 203 may then subsequently be removed by a cutting process at two portions denoted at lines X-X' as shown in FIG. 5. FIG. 7 shows a bottom view of top layer 200 after handle portion 203 was removed.

Figure 10:
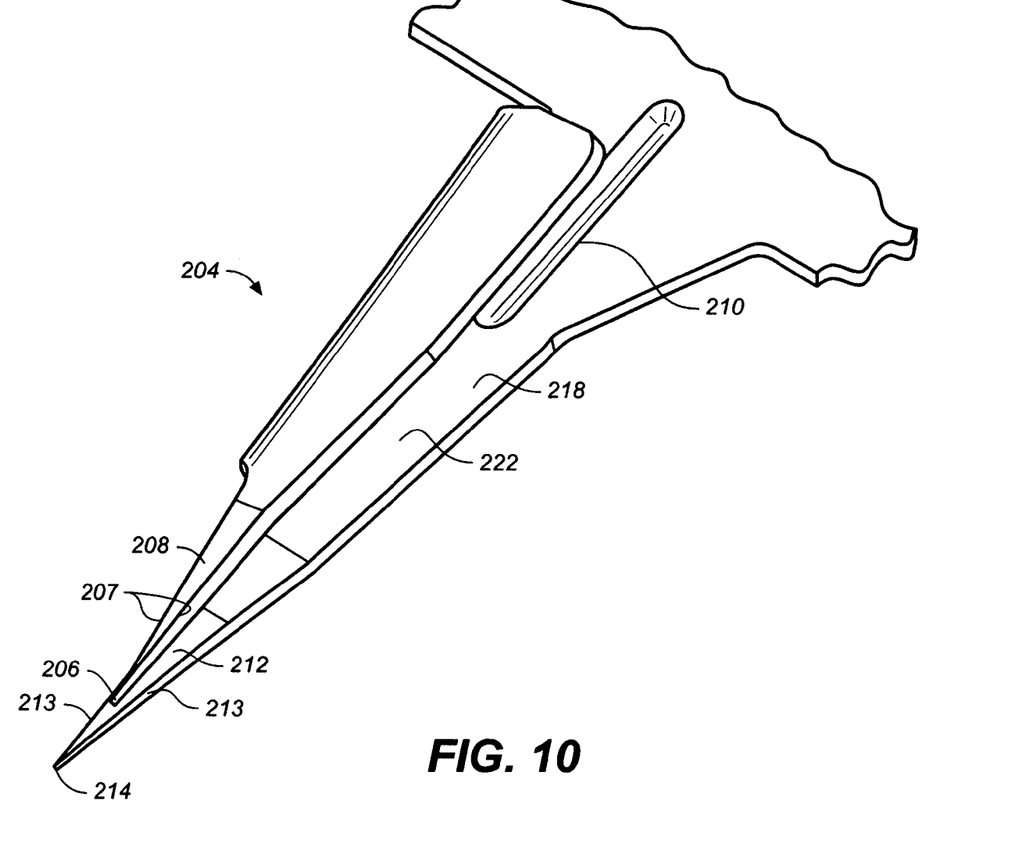
FIG. 10 is a bottom perspective view of the lance.
Figure 11:
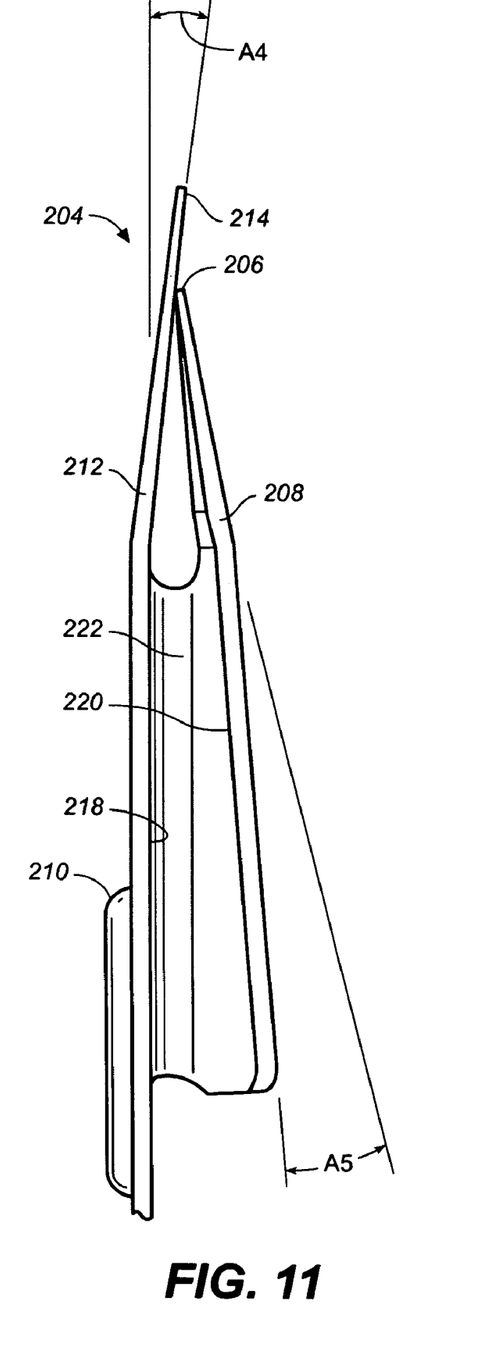
FIG. 11 is a side plan view of the lance.

FIGS. 10 and 11 show a bottom perspective view and side plan view, respectively, of lance 204 illustrating a fill channel 222. Fill channel 222 may be an open faced capillary which can be formed by an upper chamber wall 218 and lower chamber wall 220. Fill channel 222 facilitates the flow of bodily fluid from lancing element 212 to the working and the reference electrodes used for measuring an analyte. Note that, fill channel 222 may also be a connector connecting a proximal portion of lancing element 212 to a proximal portion of separation element 208. In FIG. 10, upper chamber wall 218 is connected to a proximal portion of lancing element 212 and lower chamber wall 220 is connected to a proximal portion of separation element 208.

In the present embodiment, top layer 200 may be disposed onto a base substrate 18 to form a sensor strip in a manner similar to that shown in FIG. 1. In another embodiment of this invention, a commercially available OneTouch Ultra sensor strip from LifeScan Inc. (Milpitas, Calif., U.S.A.) may be modified to adapt to top layer 200 allowing the lancing process, blood dosing process, and glucose measurement process to be integrated together.

Figure 6:
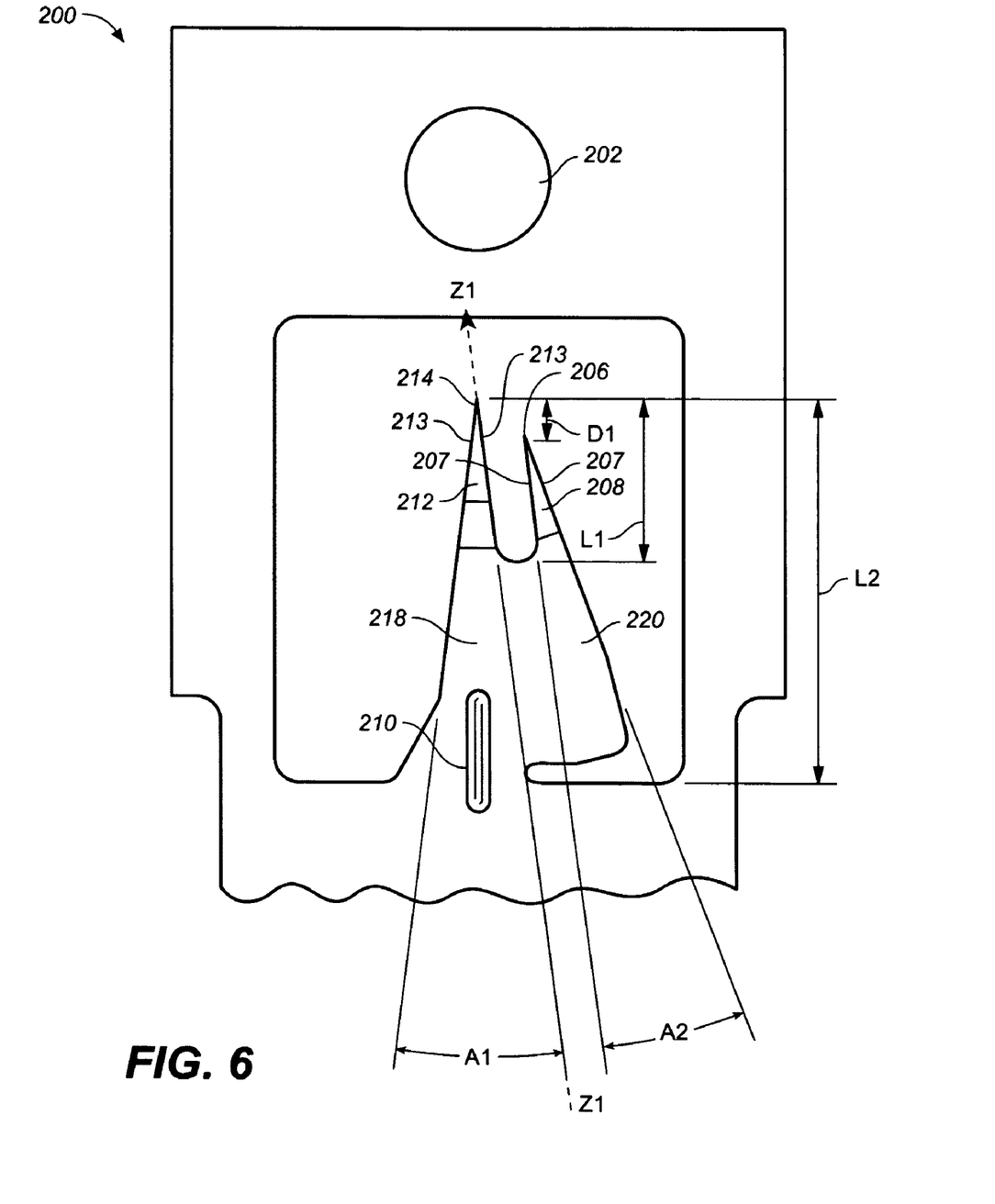
FIG. 6 is a bottom plan view of the top layer in which the lance was not folded in accordance with the embodiment shown in FIG. 4.

FIGS. 5 and 6 show a bottom plan view of top layer 200 with lance 204 in its folded and unfolded orientation, respectively. Note that the unfolded orientation may also be referred to as a flat pattern. When top layer 200 is stamped, lance 204 is in an unfolded orientation as shown in FIG. 6. In a subsequent processing step, separation element 208 and lower chamber wall 220 are folded along an axis Z1 such that they are deposed over lancing element 212 and upper chamber wall 218, respectively, as shown in FIGS. 5 and 10. In an embodiment of the present invention, lance 204 may include a separation element 208 having a separation tip 206, and a lancing element 212 having a sharpened tip 214. Note that sharpened tip 214 may also be referred to as a first sharpened end point and that separation tip 206 may be referred to as a second end point.

During the stamping process, top layer 200 can be embossed to form a stiffening rib 210. This embossing process increases the bending rigidity of conductive substrate 201 to reduce the likelihood of deforming lance 204 during the sensor strip manufacturing and handling process as well as the lancing process. In an embodiment of this invention, stiffening rib 210 may be positioned such that a portion of stiffening rib 210 is deposed on both lance 204 and main body 224. Stiffening rib 210 forms a bridge across lance 204 and main body 224 which strengthens the bending rigidity of lance 204 with respect to main body 224.

Separation tip 206 may be positioned a distance D1 from sharpened tip 214 as shown in FIGS. 5 and 6. Distance D1 may range from about 0.005 inches to about 0.020 inches. Lancing element 212 may have a length L1 which may range from about 0.06 inches to about 0.07 inches. Length L1 may be selected to be a distance which represents the approximate maximum depth in which lance 204 will penetrate the user's skin. Lance 204 may have a length L2 which represent the length L1 plus the length of fill channel 222 which transfers the bodily fluid to the working and reference electrodes. Length L2 may range from about 0.14 inches to about 0.16 inches.

Lancing element 212 and separation element 208 may respectively have a sharpness angle A1 and A2 as shown in FIG. 6. Lancing element 212 and separation element 208 may both form a triangular shape. Sharpness angle A1 may be formed by a vertex which corresponds with sharpened tip 214 and two lancing element sides 213. Similarly, sharpness angle A2 may be formed by a vertex which corresponds to separation tip 206 and two separation element sides 207. In an embodiment of the present invention, sharpness angles A1 and A2 may range from about 10° to about 25°, and preferably range from about 13° to about 14°.

In the case where sharpness angle A1 or A2 is less than about 10°, there may not be sufficient structural rigidity to prevent deformation of lancing element 212 and separation element 208 during the lancing process. For example, lance 204 may be made with a material called "stainless steel 301" which has a thickness of about 0.003 inches. In addition, when sharpness angle A1 or A2 is less than about 10°, this causes an overall width of lancing element 212 and separation element 208 to decrease and this may reduce capillarity and prevent sufficient bodily fluid from being collected. The overall width of lancing element 212 may be defined as a distance between the two lancing element sides 213 in a direction perpendicular to axis Z2. The overall width of separation element 208 may be defined as a distance between the two separation element sides 207 in a direction perpendicular to axis Z2.

Lancing element 212 may not easily puncture a user's skin when sharpness angle A1 is greater than about 25° because sharpened tip has in a sense become blunt. In such a case, if lancing element 212 was to puncture the user's skin, then the user will most likely experience an unacceptable level of pain.

Figure 8:
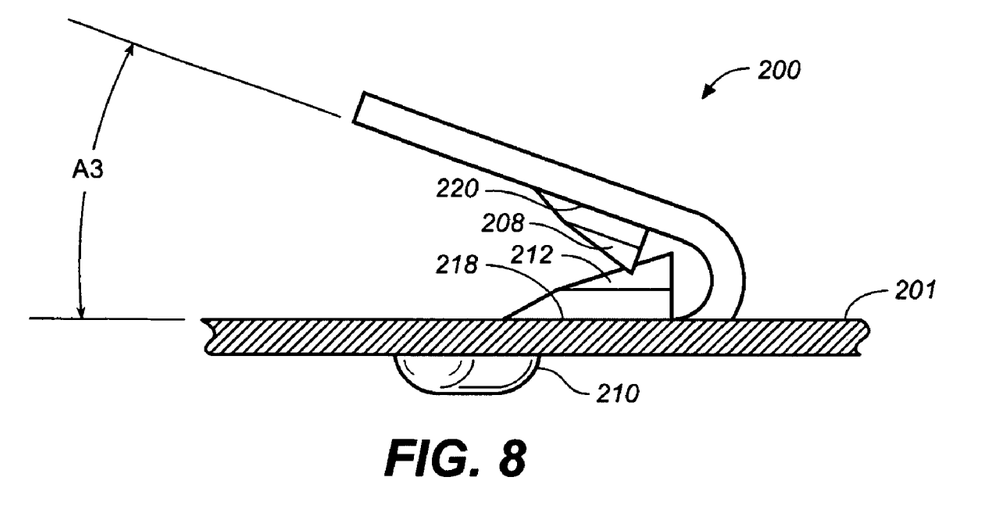
FIG. 8 is a distal plan view of the top layer of FIG. 7 taken along viewpoint 8-8.

FIG. 8 is a distal plan view of top layer 200 of FIG. 7 taken along viewpoint 8-8. The axis Z1 runs approximately parallel to a bend axis between upper chamber wall 218 and lower chamber wall 220. The bend is formed after the process in which separation element 208 and lower chamber wall 220 are folded over lancing element 212 and upper chamber wall 218. Top layer 200 has a first substantially planar portion which includes an upper chamber wall 218 as shown in FIG. 8. Top layer 200 further has a second substantially planar portion which includes a lower chamber wall 220 as shown in FIG. 8. Lower chamber wall is orientated with respect to upper chamber wall at a fold angle A3. In an embodiment of the present invention, the fold angle A3 may range from about 10° to about 30°, and preferably range from about 18° to about 22°.

Figure 9:
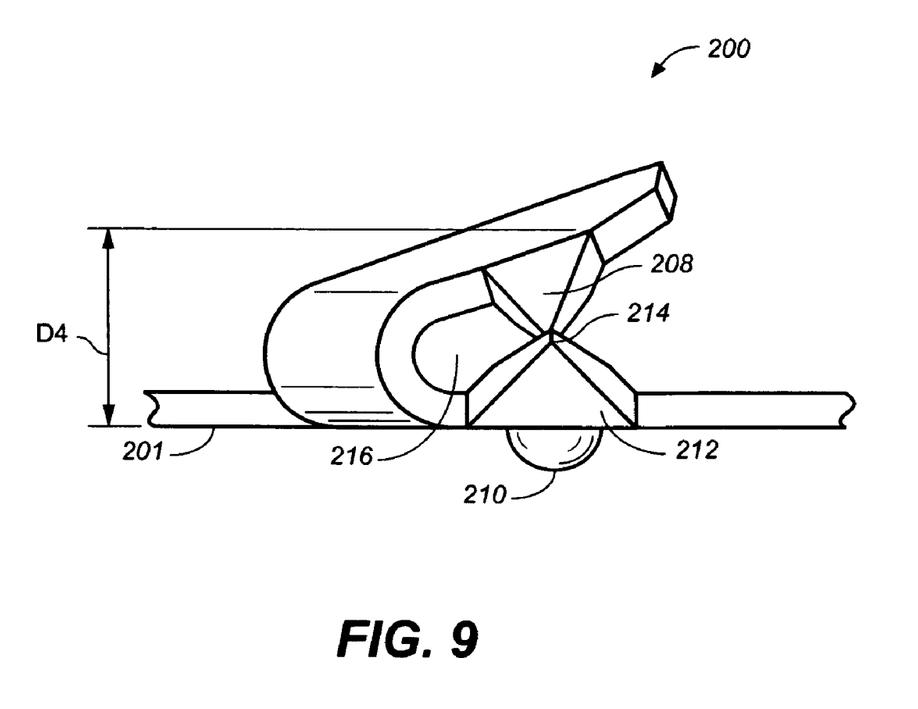
FIG. 9 is a proximal plan view of the top layer of FIG. 7 taken along viewpoint 9-9.

FIG. 9 is a proximal plan view of top layer 200 of FIG. 7 taken along viewpoint 9-9. Lance 204 further includes a gap 216 which provides an opening for bodily fluid to enter or pass through to lance 204. It is an advantage of this invention in that lance 204 is prepared from a relatively thin sheet of metal such as, for example, 0.003 inches thick which can be used to create a sufficiently large hole in a user's skin to withdraw a sufficient volume of bodily fluid. For example, if lance 204 was not folded over, it would create a wound size that would be limited in one dimension to be no more than 0.003 inches thick. In an embodiment of this invention, constructing lance 204 to have a fold angle A3 of about 20° increased the one dimension of the wound size to range from about 0.012 inches to about 0.014 inches as shown as a distance D4 in FIG. 9.

FIG. 9 also illustrates that sharpened tip 214 provides a leading point for piercing a user's skin and that separation tip 206 is tucked under lancing element 208. Thus, because of the positioning of separation tip 206, it does not pierce a user's skin after sharpened tip 214 penetrates the user's skin. If separation tip 206 was orientated in a manner that caused it to pierce the user's skin in addition to lancing element 208, this would cause lance 204 to require additional force for piercing the user's skin. Therefore, in one embodiment of this invention, separation element 208 may be sufficiently bent towards lancing element 212 such that lancing element 212 protects separation tip 206 from piercing the user's skin. In another embodiment of this invention, lancing element 212 may be sufficiently bent towards separation element 208 such that lancing element 212 protects separation tip 206 from piercing the user's skin.

FIG. 11 is a side plan view of the lance which illustrates a lancing element angle A4 and a separation element angle A5. Lancing element angle A4 may be formed by a plane substantially coincident with upper chamber wall 218 and a plane substantially coincident with lancing element 212. In an embodiment of the present invention, lancing element angle A4 may range from about 5° to about 15°, and preferably be about 8°. Separation element angle A5 may be formed by a plane substantially coincident with lower chamber wall 220 and a plane substantially coincident with separation element 208. Upper chamber wall 218 and lower chamber wall 220 may be configured such that they are approximately parallel to each other. In an embodiment of the present invention, separation element angle A5 may range from about 0° to about 15°, and preferably be about 8°.

Figure 12:
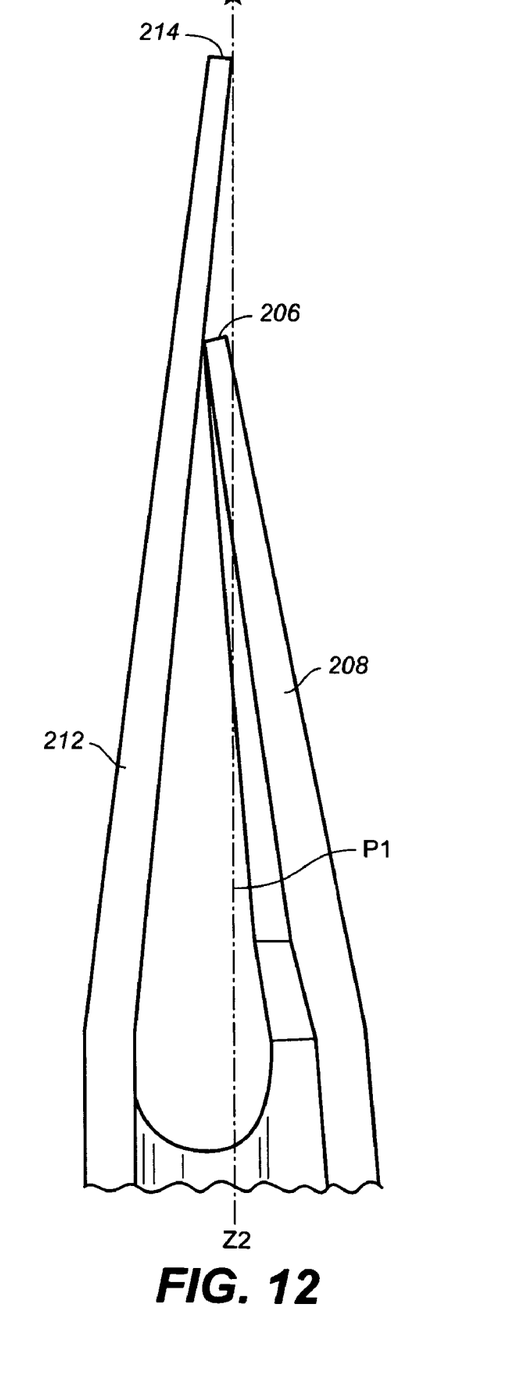
FIG. 12 is an expanded side plan view of the lance.

FIG. 12 is an expanded side plan view of the lance which illustrates a position of sharpened tip 214 and separation tip 206 relative to axis Z2. Axis Z2 may represent an approximately center position of lance 204 that coincides with sharpened tip 214. In addition, axis Z2 may also represents a direction in which lance 204 moves when launched towards the user's skin. The direction indicated by axis Z2 may be approximately perpendicular to a surface of the user's skin when lance 204 is about to be launched.

In an embodiment of this invention, separation element 208 may cross-over a plane P1 coincident with sharpened tip 214 and parallel to upper chamber wall 218. In this embodiment, separation tip 206 may be on a side of plane P1 closer to lancing element 212. Separation tip 206 may be either touching lancing element 212 or near lancing element 212 so long as separation tip 206 is on the side of plane P1 closer to lancing element 212. It is an advantage of this embodiment in that separation tip 206 does not pierce the user's skin because it is tucked under and protected by lancing element 212.

In another embodiment of this invention, separation tip 206 may be partially on a side on a side of plane P1 closer to lancing element 212. Note, that it is possible to have only a portion of separation tip 206 on a side of plane P1 closer to lancing element 212 because separation tip 206 has a finite size. In this embodiment, the separation tip 206 will be partially entering an existing wound created by the lancing element 212 which allows lancing element 212 to partially protect separation tip 206.

In an embodiment of this invention, lance 204 is launched towards a user's skin. Initially, sharpened tip 214 will pierce or puncture the user's skin to form a wound. Next, lancing element 212 will continue to move into the user's skin causing the wound to expand because the two lancing element sides 213 are slicing the user's skin and spreading the wound. After lancing element 212 has entered the wound, separation element 208 will continue to move in the user's skin also causing the wound to further expand. In addition, the two separation element sides 207 can also slice the user's skin facilitating the expansion and spreading of the wound. Once the wound is sufficiently large, bodily fluid can flow from a distal end of lance 204 to fill channel 222 and then to a working electrode and a reference electrode used for measuring an analyte. Factors that can cause separation element 208 to increase the amount of wound spreading are an increase in sharpness angle A2, fold angle A3, and/or separation angle A5.

However, there may be an unacceptable level of pain if the spreading of the wound became too large. When the wound has been sufficiently spread, fluid can flow from a distal end of lance 204 to a proximal end of fill channel 222.

In an alternative embodiment to this invention, separation tip 206 can be made dull or blunt because it is not used for piercing the user's skin as long as separation element is tucked under and protected by lancing element 212 during the lancing process.

It will be recognized that equivalent structures may be substituted for the structured illustrated and described herein and that the described embodiment of the invention is not the only structure which may be employed to implement the claimed invention. In addition, it should be understood that every structure described above has a function and such structure can be referred to as a means for performing that function.

While preferred embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A lance comprising:
    a lancing element having a sharpened tip;
    a separation element having a separation tip, wherein said separation tip is positioned proximal to said sharpened tip and wherein said lancing element protects said separation tip from initiating a puncture when launching said lance into a user's skin;
    a connector connecting a proximal portion of said lancing element to a proximal portion of said separation element, said connector forming a fill channel, wherein said fill channel comprises an upper chamber wall and a lower chamber wall, wherein said upper chamber wall is orientated with respect to said lower chamber wall to form a fold angle, wherein said fold angle ranges from about 10° to about 30°.

2. The lance according to claim 1, wherein said lancing element has a sharpness angle formed by two lancing element sides, wherein said two lancing element sides converge at a vertex coincident with said sharpened tip, said sharpness angle ranging from about 10° to about 25°.

3. The lance according to claim 1, wherein said lancing element, said separation element and said fill channel are formed from a single sheet of metal.

4. The lance according to claim 1, wherein a space between said lancing element and said separation element forms a gap, said gap increasing in size proximal to said separation tip.

5. The lance in accordance with claim 1, wherein a proximal end of said fill channel is integrated into a sensor strip.

6. A lance comprising:
    a lancing element having a sharpened tip;
    a separation element having a separation tip, wherein said separation tip is positioned proximal to said sharpened tip and wherein said lancing element protects said separation tip from initiating a puncture when launching said lance into a user's skin;
    a connector connecting a proximal portion of said lancing element to a proximal portion of said separation element, said connector forming a fill channel, wherein said fill channel comprises an upper chamber wall and a lower chamber wall,
    said upper chamber wall being connected to a proximal portion of said lancing element,
    said lower chamber wall being connected to a proximal portion of said separation element,
    said lance having a plane approximately parallel to said upper chamber wall and coincident with said sharpened tip,
    wherein said separation tip is positioned on a side of said plane closer to said upper chamber.

7. The lance according to claim 6, wherein said lancing element has a sharpness angle formed by two lancing element sides, wherein said two lancing element sides converge at a vertex coincident with said sharpened tip, said sharpness angle ranging from about 10° to about 25°.

8. The lance according to claim 6, wherein said lancing element, said separation element and said fill channel are formed from a single sheet of metal.

9. The lance according to claim 6, wherein a space between said lancing element and said separation element forms a gap, said gap increasing in size proximal to said separation tip.

10. The lance in accordance with claim 6, wherein a proximal end of said fill channel is integrated into a sensor strip.

11. A sensor strip comprising:

A lance comprising:

a lancing element having a sharpened tip;

a separation element having a separation tip, wherein said separation tip is positioned proximal to said sharpened tip and wherein said lancing element protects said separation tip from initiating a puncture when launching said lance into a user's skin;

a connector connecting a proximal portion of said lancing element to a proximal portion of said separation element, said connector forming a fill channel, a main body; wherein said lance and said main body are formed from a single sheet of material, wherein a proximal end of said lance connects to a distal end of said main body, and a rib, wherein said rib is an embossment of said single sheet of material and said rib is deposed on a portion of said proximal end of said lance and on a portion of said distal end of said main body, whereby said rib strengthens a bending rigidity of said lance with respect to said main body.

* * * * *